United States Patent [19]
Bischof et al.

[11] Patent Number: 5,720,743
[45] Date of Patent: Feb. 24, 1998

[54] THERMALLY INSULATING SURGICAL PROBE

[76] Inventors: John C. Bischof, 1838 Sargent Ave., St. Paul, Minn. 55105; Nir Merry, 1727 Cherrytree La., Mountain View, Calif. 94040; John Hulbert, 7721 Tara Rd., Edina, Minn. 55435

[21] Appl. No.: 661,410

[22] Filed: Jun. 7, 1996

[51] Int. Cl.⁶ .................................... A61B 17/00
[52] U.S. Cl. ...................... 606/1; 606/20; 606/32; 607/98
[58] Field of Search .................. 606/20–30, 1, 606/32, 34; 607/98, 99, 105, 113, 116; 128/846

[56] References Cited

U.S. PATENT DOCUMENTS

| | | | |
|---|---|---|---|
| 4,022,215 | 5/1977 | Benson | 606/23 |
| 4,202,336 | 5/1980 | Van Gerven | 606/21 |
| 4,655,494 | 4/1987 | Eads et al. | 294/49 |
| 5,117,822 | 6/1992 | Laghi | 607/105 |
| 5,234,004 | 8/1993 | Hascoet et al. | 607/116 |
| 5,326,343 | 7/1994 | Rudie et al. | 607/102 |
| 5,330,518 | 7/1994 | Neilson et al. | 607/102 |
| 5,531,676 | 7/1996 | Edwards et al. | 607/113 |

*Primary Examiner*—Jennifer Bahr
*Assistant Examiner*—David Ruddy

[57] ABSTRACT

A surgical probe having the ability to thermally insulate adjacent healthy tissue from cooling or heating effects at adjacent tissue being subjected to thermal destruction by cryosurgery, electrosurgery and hyperthermia. The probe includes a spatula shaped thermally insulating member that is mounted at the distal end of an elongated rigid member of a width sized for insertion through a small cutaneous incision. The insulating spatula is of a material transparent to ultrasound thus allowing ultrasonic imaging of tissue through the thermal insulator without substantial image deterioration.

13 Claims, 3 Drawing Sheets

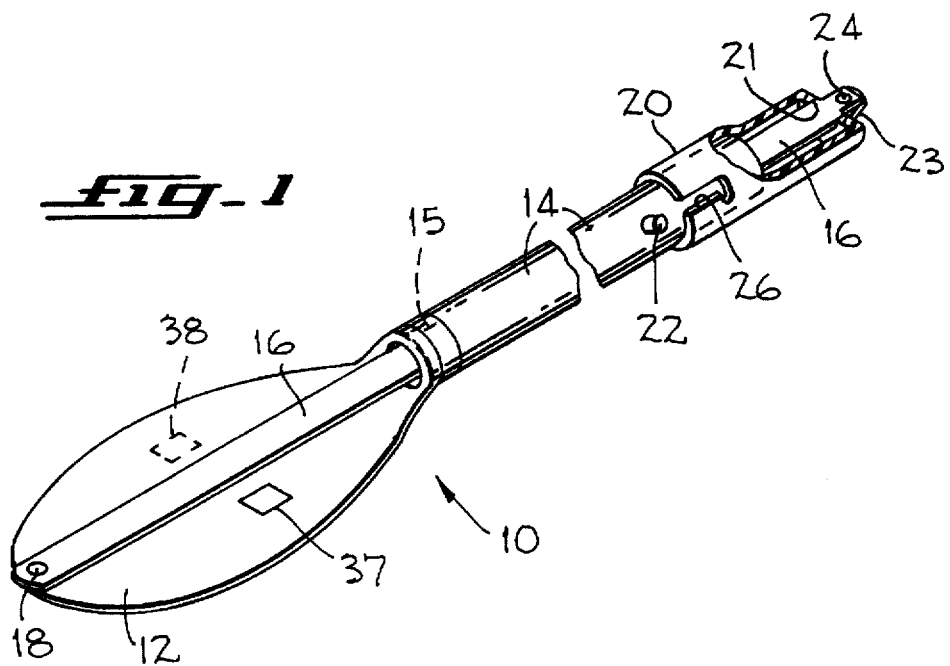
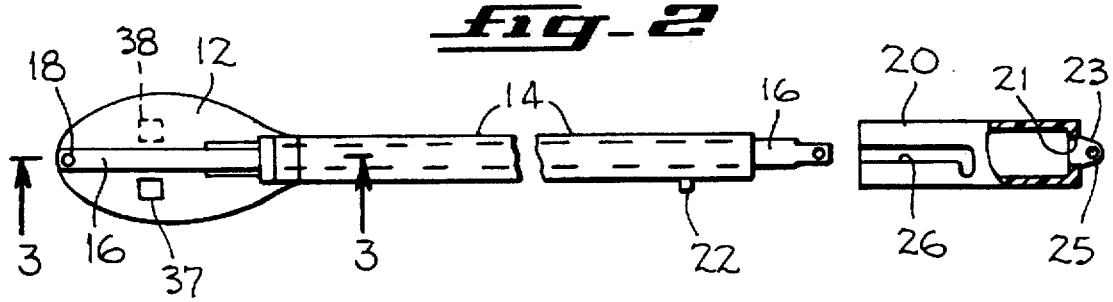
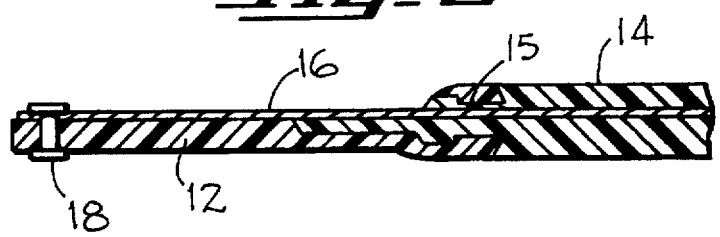

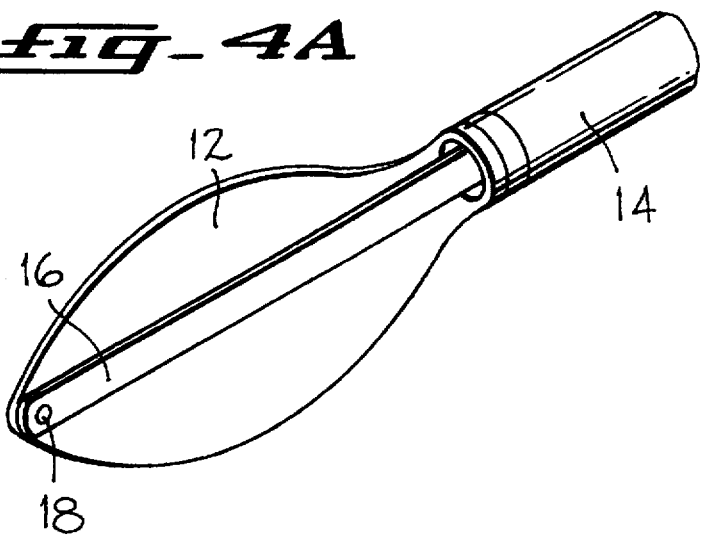
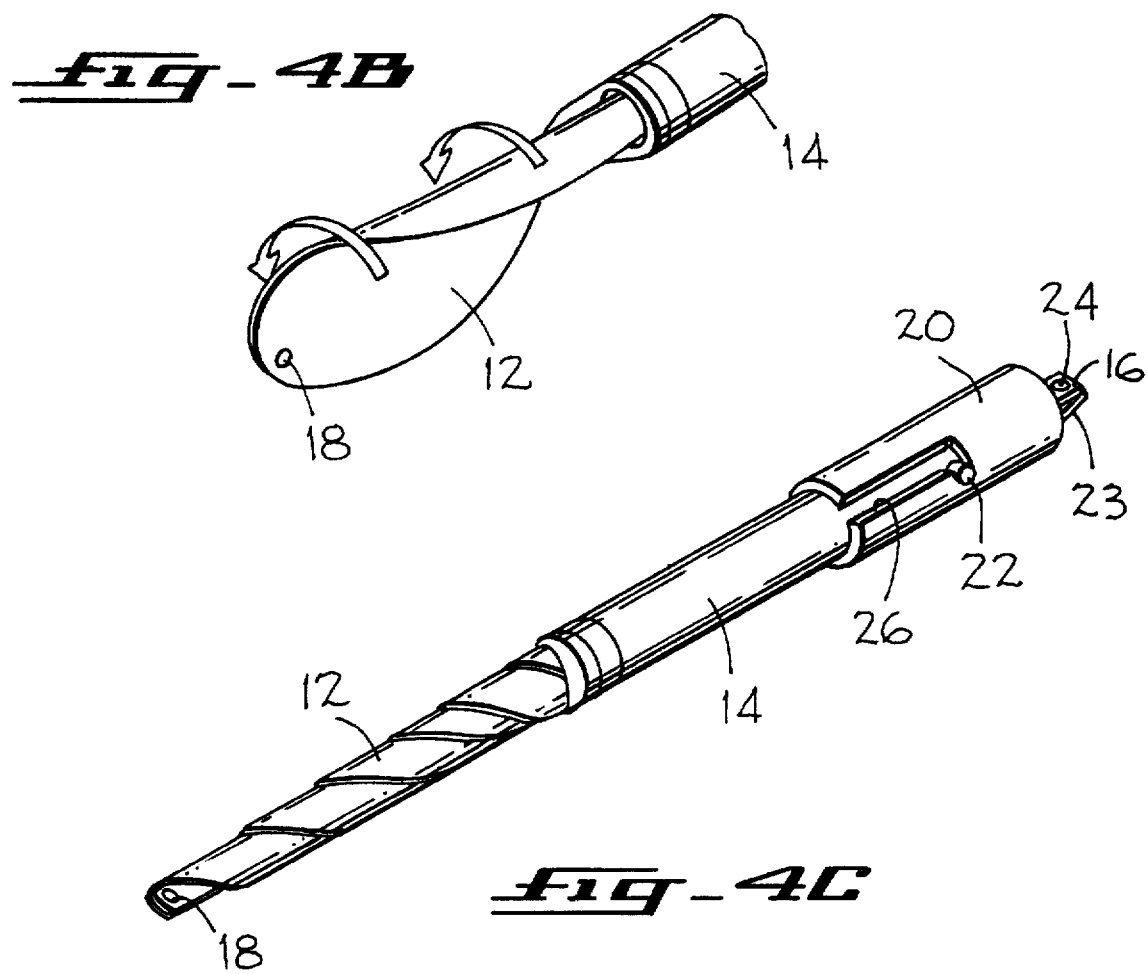

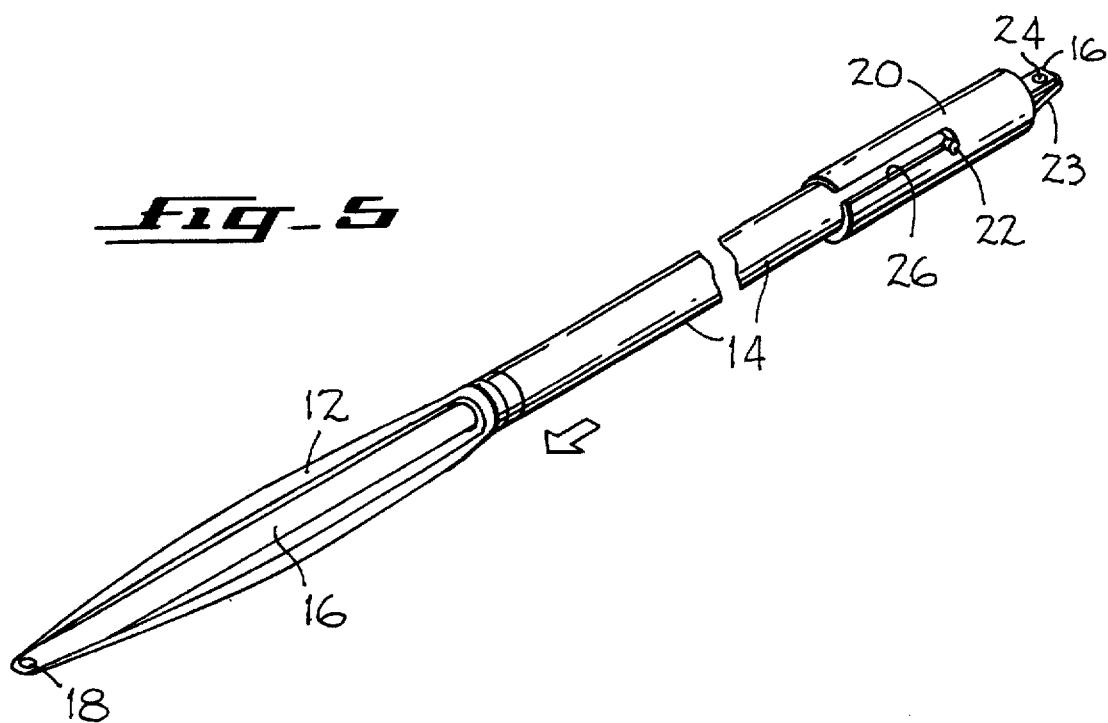
_fig_5
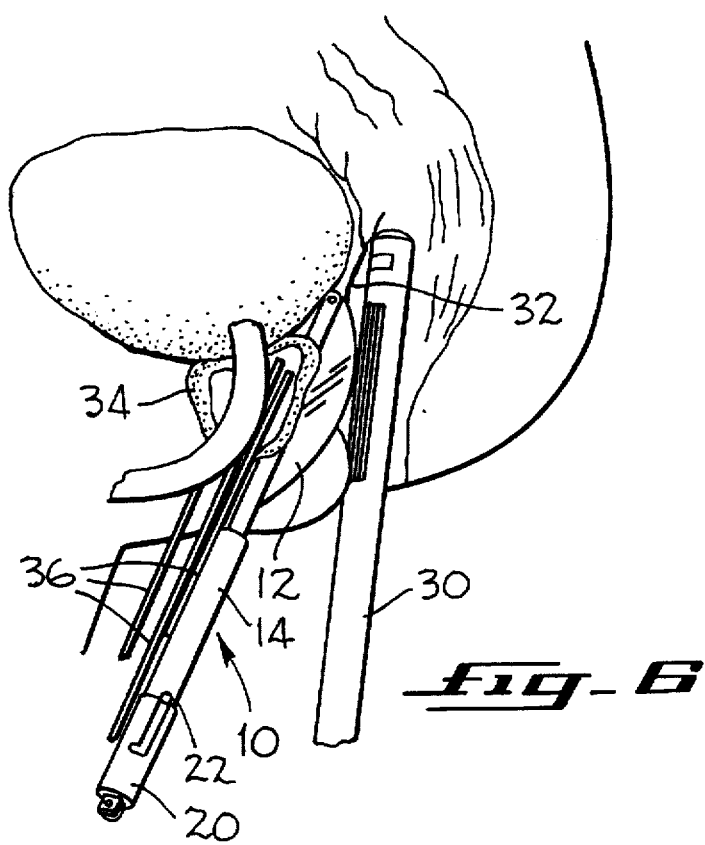
_fig_6

THERMALLY INSULATING SURGICAL PROBE

BACKGROUND OF THE INVENTION

1. Field of the Invention

The present invention generally to a device in use in cryosurgical, electrosurgical and hyperthermia situations. More particularly, the invention involves a surgical instrument that has the ability to thermally insulate bodily tissue from exposure to extreme temperature imposed by surgical procedures such as cryosurgery, electrosurgery and hyperthermia.

2. Description of the Prior Art

Treatment of tissue affected by cancer can be performed by multiple means such as cryosurgery and electrosurgery. Cryosurgical apparatus such as described in U.S. Pat. No. 4,946,460 which uses liquid nitrogen cryogenic is refrigerant and cryosurgical apparatus described in U.S. Pat. No. 4,519,389 which uses semiconductor cooling elements are used for hypothermic tissue destruction in the treatment of cancer and other non-desirable tissue. Electrosurgical apparatus such as described in U.S. Pat. No. 4,936,301 and in U.S. Pat. No. 4,943,290 are used for hyperthermic tissue destruction.

A common problem encountered during surgical procedures involving cryosurgery, electrosurgery and hyperthermia is the unwanted destruction of adjacent healthy tissue. Such side effects can lead to medical complications and result in longer hospitalization and/or a need for further surgical correction. As an example, during cryosurgical treatment of prostate cancer, the entire prostate is cooled to temperatures well below the freezing point of tissue. It is observed that the rectal wall which is typically in contact with the frozen prostate can suffer tissue damage such as the formation of rectal fistulas.

In addition, to maximize the effectiveness of cryosurgery, it is desirable to isolate the treated tissue, thus allowing a more effective freeze to a lower end temperature of the target tissue. Isolating the target tissue guarantees that the cryosurgical effect is focused only on the tissue to be destroyed.

It is customary to use ultrasound imaging during a cryosurgery to monitor and control the procedure intraoperatively. Ultrasound is used first to determine size and extent of the target tissue or tumor to be frozen. The ultrasound imaging can then be used in guiding the placement of the cryosurgical probes which deliver the freezing effect to the tissue. Finally, ultrasound imaging can monitor the size and extent of the freezing which is induced from the cryoprobes during a procedure. It is proposed that ultrasound imaging will be utilized intraoperatively to assist in the placement of the insulating probe between the treated tissue and the surrounding healthy tissue. Also, it is proposed that the insulating material will be of a material which allows ultrasound imaging through it without substantial image deterioration.

Therefore, there is a need for a thermally insulating surgical instrument designed to protect healthy tissue from the effects of cryosurgical, electrosurgical and hyperthermia treatment and having the property of not obstructing ultrasonic imaging in the region surrounding the tissue under treatment.

SUMMARY OF THE INVENTION

The object of the present invention is to provide a method and instrument which will enable protection of healthy tissue from the effects of cryosurgery, electrosurgery and hyperthermia while enhancing the effectiveness of the treatment of the target tissue.

Another objective of the invention is to provide a thermally insulating probe having the ability to be reconfigured for simple insertion and placement through a small cutaneous incision, optionally using laparoscopic surgery and ultrasonic guidance.

Yet another objective of the invention is to provide a thermal insulator having the ability to be placed between the target tissue and an ultrasound transducer not hindering the ultrasonic imaging of the target tissue.

The invention disclosed herein relates to a thermal insulation probe for percutaneous insertion in thermal surgical procedures and for positioning between tissue to be thermally destroyed and immediately adjacent tissue to be protected from the effects of the thermal surgery. A thermal insulator provides a heat flow barrier and a handle is attached to one end of the thermal insulator. Means is provided for alternatively configuring the thermal insulator in a heat flow barrier condition and a reduced cross section dimension condition. The means for configuring the thermal insulator is attached to the other end of the thermal insulator. When the thermal insulator is in the reduced cross section configuration it may be inserted into and withdrawn from the body.

In another aspect of the invention, a thermal insulation probe is provided for percutaneous positioning between tissue to be thermally destroyed and adjacent tissue to be protected. A flexible flat thin thermal barrier has a handle attached to one end thereof, wherein the handle has a longitudinal channel. A stiffening member extends through the channel and is attached to the opposite end of the thermal barrier. The stiffening member is movable between a position extending from the channel, wherein the thermal barrier is stretched taut, and a nonextended relaxed position, wherein the thermal barrier assumes the flat thin shape. Releasable latching means is provided for securing the stiffening member in the extended position and for releasing the stiffening member to assume the nonextended relaxed position.

The method of the present invention involves protecting a first internal body tissue from thermal destruction during thermal surgical destruction of a second adjacent body tissue using a flat flexible thermal barrier configurable in an open flat condition and a closed elongate condition. The thermal barrier is configured in a closed elongate condition so that the cross section dimensions thereof are reduced. The thermal barrier in reduced cross section condition is inserted into the body to a position between the first and second body tissues prior to the thermal surgical procedure. The thermal barrier is then disposed in the open flat condition between the first and second body tissues during the thermal surgical procedure.

BRIEF DESCRIPTION OF THE DRAWINGS

FIG. 1 is a perspective view of the insulating probe of the present invention.

FIG. 2 is a plan view of the surgical probe of the present invention.

FIG. 3 is a section view along the line 3—3 of FIG. 2.

FIG. 4C is a perspective view showing the insulator in spiraled condition.

FIG. 4B is a perspective view showing spiraling of the thermal insulator of the present invention.

FIG. 4A is a perspective view of the distal end of the present invention.

FIG. 5 is a perspective view showing the insulator in extended condition.

FIG. 6 is a section view showing a portion of the male anatomy being subjected to a prostate cryosurgery.

DESCRIPTION OF THE INVENTION

Referring to the drawings and particularly to FIGS. 1 through 3, one form of the insulating surgical probe of the present invention is thereshown. The insulating probe, generally designated by the numeral 10 includes a flat silicone rubber insulator 12 connected at the distal end of an elongated cylindrical shaped handle 14. The insulator may be attached to handle 14 by molding one end of the insulator into a groove 15 on the handle distal end. The groove 15 is shaped to hold one end of the insulator 12 both axially and rotationally.

In the preferred embodiment shown in FIGS. 1-3 the handle housing 14 is shown wherein insulator 12 is attached to and extends from the distal end of the handle and is riveted at the extended end to a stiffening member 16 via a rivet 18. The stiffening member 16 may be a flat stainless steel strip.

In the preferred embodiment shown in FIG. 1, a member 20, termed the rear locking cap, is linked to the stiffening member at the other end thereof by means of a plastic rivet 24. Locking cap 20 has a slot 21 in the end thereof shaped to pass the end of the stiffening member 16. A tab 23 extends from the cap adjacent to the slot 21. The tab has a through hole 25 which accepts the rivet 24. Cap member 20 is also provided with an elongated "L" shaped slot 26 which locks locking cap member 20 longitudinally with respect to handle member 14 when the locking cap is slid forward on the handle and rotated relative to the handle to position a handle mounted pin 22 in the bottom or blind segment of the "L" shaped slot.

Insulator member 12 can be constructed from a wide variety of different materials and can be shaped in numerous configurations to enable optimal delivery, placement and tissue insulation. For example, member 12 can be constructed of a material which is thermally insulating, elastic and substantially permeable to ultrasound energy, such as silicone rubber.

Member 14, the probe handle, can be constructed from a wide variety of different materials and can be shaped in numerous configurations. For example, member 14 can be constructed of any stiff material such as rigid plastic or stainless-steel coated with Teflon.

The insulator 12 is characterized as a flat spatula or oval shaped flexible member. One feature of the present invention relates to the insulator 12 being reconfigurable in shape (reduced cross section) by stretching and/or wrapping (spiraling) the insulator 12 for the purpose of both efficient and convenient delivery and placement as well as removal from the surgical site through a small cutaneous incision. The insulator reconfiguration is accomplished by extending and/or rotating stiffening member 16 which extends through housing 14 thus stretching and/or spirally wrapping insulator 12 around the stiffening member 16. In the instance where the stiffening member 16 is only extended through an axial slot in handle housing 14 (FIG. 5), the handle is inserted deeper into the locking cap 20 and the cap is rotated to lock the stiffening member 16 in extended position and the insulator 12 is in a stretched (small cross section) condition as shown. In such a case a slot through handle 14 to allow passage of stiffening member 12 is sufficient. In the instance where the insulator 12 is wrapped spirally about the stiffening member 16 as seen in FIGS. 4a–4c, a passage through handle 14 sufficient in cross section to allow rotation of the member 16 within the handle 14 is required; i.e., a circular cylindrical passage through handle 14. In such a case cap 20 and therefore the member 16 is rotated within the handle 14 until a sufficiently small cross section of insulator 12 is obtained and the cap 20 is locked to handle 14 by means of slot 26 and pin 22 as described hereinbefore.

OPERATION

In accordance with standard practices of cryosurgical and electrosurgical procedures, the surgeon will use ultrasound imaging to study and monitor the location of the operating devices. This is seen in FIG. 6 as represented by the ultrasound probe 30 positioned within the rectum. In the case of delivery of the device of this invention to protect the rectum wall 32 from cryosurgical freezing in the prostate 34 (FIG. 6), it is important to insure device placement to avoid injury to the rectum which is in intimate proximity to the prostate.

A percutaneous technique can be used which utilizes a balloon placed under ultrasound guidance into the perineum between the rectum and prostate. The balloon can then be gently inflated with an endoscope inside the balloon. This would enable the space to be scrutinized prior to surgical device placement.

Alternatively to the balloon assisted placement, a small perineal incision can be made and the space between the rectum and the prostate can be dissected in an open surgical fashion. In either the balloon or open surgical approach, after the space between the rectum and prostate has been created, the device 10 of the present invention will be inserted via a transperineal incision and placed as shown in FIG. 6 under ultrasound guidance or direct vision. During the delivery of the thermally insulating surgical probe it will be in an elongated and/or wrapped configuration to minimize the outer diameter of the device as shown in FIGS. 5 and 4a–4c respectively.

After placement of the insulator probe 10 at the appropriate location, the insulator 12 will be unwrapped and/or allowed to contract to its full open position which will then maximize insulation coverage and therefore provide thermal protection for the rectum wall.

Once the insulator 12 is in position, the cryosurgical probes 36 (FIG. 6) can be placed under ultrasound imaging lo guidance into the effected tissue location. Once all the cryoprobes are in place, the cryogenic refrigerant is allowed to flow into the probes thus freezing the undesirable tissue. Optimally, the surgeon will be able to monitor prostate exterior and rectal wall temperatures by means of temperature sensors 37 and 38 positioned on opposing sides of the insulator 12 as seen in FIGS. 1 and 2.

The same delivery technique utilizing the disclosed invention can be used to protect a variety of tissues and organs during other thermal surgeries or electrosurgeries. FIG. 6 simply outlines one example involving cryosurgery of the prostate where the adjacent rectum wall is particularly sensitive to thermal damage.

Although the best mode contemplated for carrying out the present invention has been herein shown and described, it will be understood that modification and variation may be made without departing from what is regarded to be the subject matter of the invention.

What is claimed is:

1. A thermal insulating probe for use in cryosurgery and electrosurgery comprising a spatula shaped thermal insulator, an elongated insertion handle attached to said thermal insulator, and means attached between said thermal insulator and said insertion handle for configuring said thermal insulator alternatively in thermally protective and percutaneous insertion configurations.

2. A probe as defined in claim 1 in which said thermal insulator comprises material transparent to ultrasound energy allowing ultrasound imaging through it.

3. A probe as defined in claim 1 comprising temperature sensing elements embedded on at least one side of said thermal insulator.

4. A thermal insulation probe for percutaneous insertion in thermal surgical procedures and for positioning between tissue to be destroyed and immediately adjacent tissue to be protected from the effects of the thermal surgery, comprising a thermal insulator for providing a heat flow barrier across a predetermined area, a handle attached to one end of said thermal insulator, and means for alternatively configuring said thermal insulator for providing an open heat flow barrier configuration and a reduced cross section configuration, said reduced cross section configuration providing ease of percutaneous insertion and withdrawal of said thermal insulator, said last named means being attached to an opposite end of said thermal insulator.

5. A thermal insulation probe as in claim 4 wherein said thermal insulator is an elastic member, and wherein said means for alternatively configuring said thermal insulator, comprises a stiffening member attached to said opposite end of said thermal insulator and extending through said handle, means mounted on said handle disposed for sliding movement along a portion of the length of said handle and attached to said stiffening member, and latching means for securing said means mounted on said handle in extended condition from said handle, whereby said thermal insulator is stretched elastically in said reduced cross section configuration.

6. A thermal insulation probe as in claim 4 wherein said handle has a longitudinal channel and wherein said means for alternatively configuring said thermal insulator, comprises an elongate member extending through said longitudinal channel and attached at one end to said opposite end of said thermal insulator, and means mounted on said handle for rotation therewith attached to the other end of said elongate member, whereby rotation of said last named means disposes said thermal insulator in a spirally wrapped configuration providing said reduced cross section configuration.

7. A thermal insulation probe as in claim 4, comprising a first temperature sensor attached to one side of said thermal insulator, and a second temperature sensor attached to the opposing side of said thermal insulator, whereby the temperatures of the tissues to be destroyed and to be protected are monitored.

8. A thermal insulation probe for percutaneous positioning between tissue to be thermally destroyed and adjacent tissue to be protected, comprising a flexible flat thin thermal barrier, a handle attached to one end of said thermal barrier, said handle having a longitudinal channel, a stiffening member extending through said channel attached to the opposite end of said thermal barrier, whereby said stiffening member is movable between a position extending from said channel, and thereby stretching said thermal barrier between said one end and said opposite end, and a relaxed position, and releasable latching means for securing said stiffening member in said position extending from said channel and for releasing said stiffening member to assume said relaxed position.

9. A thermal insulation probe as in claim 8 comprising temperature sensors on opposing flat sides of said thermal barrier, whereby temperature of tissue to be destroyed and tissue to be protected is monitored.

10. A method of protecting a first internal body tissue to be protected from thermal destruction of a second internal body tissue to be destroyed during a thermal surgical procedure using a flat flexible thermal barrier configurable in an open flat condition and a closed elongate condition, comprising the steps of configuring the thermal barrier in the closed elongate condition, thereby reducing the cross section dimensions of the thermal barrier, inserting the reduced cross section thermal barrier into the body to a position between the first and second body tissues prior to the thermal surgical procedure, and configuring the thermal barrier in the open flat condition in the position between the first and second internal body tissues.

11. The method of claim 10 comprising the additional steps of configuring the thermal barrier in the closed elongate condition a second time following the thermal surgical procedure, and withdrawing the reduced cross section thermal barrier from the body.

12. The method of claim 10 comprising the step of monitoring the temperature of the first internal body tissue during the thermal surgical procedure.

13. The method of claim 10 comprising the step of monitoring the temperature of the second internal body tissue during the thermal surgical procedure.

* * * * *